United States Patent
Raijmakers et al.

(10) Patent No.: US 7,773,777 B2
(45) Date of Patent: Aug. 10, 2010

(54) SYSTEM FOR PROVIDING A PERSONALIZED EXPERIENCE TO A PERSON IN A MEDICAL ENVIRONMENT

(75) Inventors: Jozef Hieronymus Maria Raijmakers, Eindhoven (NL); Laszlo Csaba Herczegh, Eindhoven (NL); Alex Wee Kar Tan, Eindhoven (NL); Tom Philippe Jean Jacques Delaey, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 1043 days.

(21) Appl. No.: 10/580,496

(22) PCT Filed: Nov. 11, 2004

(86) PCT No.: PCT/IB2004/052381

§ 371 (c)(1),
(2), (4) Date: May 23, 2006

(87) PCT Pub. No.: WO2005/051471

PCT Pub. Date: Jun. 9, 2005

(65) Prior Publication Data
US 2007/0176920 A1 Aug. 2, 2007

(30) Foreign Application Priority Data
Nov. 26, 2003 (EP) .................................. 03104375

(51) Int. Cl.
*G06K 9/00* (2006.01)
*G06F 17/00* (2006.01)
*G06Q 10/00* (2006.01)

(52) U.S. Cl. ........................ 382/115; 382/128; 345/418; 705/2

(58) Field of Classification Search ................. 382/115, 382/128; 705/2, 3; 455/556.1; 2/114; 607/107, 607/104, 108; 345/419, 418; 378/196; 600/27, 600/26, 28; 160/10
See application file for complete search history.

(56) References Cited

U.S. PATENT DOCUMENTS

| 4,319,840 | A  | * | 3/1982  | Kondo et al. ............. 356/241.1 |
| 5,184,190 | A  | * | 2/1993  | Rai et al. ................. 356/239.1 |
| 6,503,188 | B1 | * | 1/2003  | August ....................... 600/27 |
| 6,641,522 | B2 | * | 11/2003 | August ....................... 600/27 |
| 6,764,743 | B2 | * | 7/2004  | Kato et al. ................... 428/118 |
| 6,870,673 | B2 | * | 3/2005  | Cromer et al. ............... 359/450 |
| 2002/0038073 | A1 | | 3/2002 | August |

FOREIGN PATENT DOCUMENTS

| DE | 4242258 A1 | 4/1994 |
| EP | 0938866 A1 | 9/1999 |

* cited by examiner

*Primary Examiner*—Sheela C Chawan

(57) ABSTRACT

Through changes in lighting and audio solutions together with projections of images and/or animations that are initiated by the entrance of a person (professional or patient) in a medical environment, such as a radiology department, cardiology department, intensive care unit, etc., a certain ambience/atmosphere is created in this specific architectural context. This ambience can be a choice from certain predefined themes (e.g. animal drawings for children or nature images) or truly personal when personal content (e.g. images of family or vacation) is inserted in the system.

10 Claims, 3 Drawing Sheets

Figure 1:

SYSTEM FOR PROVIDING A PERSONALIZED EXPERIENCE TO A PERSON IN A MEDICAL ENVIRONMENT

The invention relates to a system for providing a personalized experience to a person in a medical environment.

The invention furthermore relates to a method of providing a personalized experience to a person in a medical environment.

A person coming to a hospital for a certain medical treatment or examination usually does not feel comfortable and at ease. This is caused for example by anxiety and by the fact that the person is unfamiliar with the professional medical environment and the treatment or examination that has to be carried out. This may especially be the case with small children or older people. These negative emotions of the patient may hinder the correct carrying out of the treatment or examination, thus making it necessary for the medical staff to spend more time calming and reassuring each individual patient before and during the examination or treatment. In this manner the efficiency of the workflow is negatively influenced.

It is an object of the invention to make the medical environment more comfortable for patients. To achieve this object, a system according to the invention comprises a system for providing a personalized experience to a person in a medical environment, comprising selection means for selecting preferred data from a collection of data, connected with control means, for controlling display means for displaying the selected data in the medical environment. Before entering a certain medical environment, such as an examination room in a hospital, the patient is offered the possibility to select certain data from a collection of data, based on his or her own personal preferences, via the selection means. These data may comprise for example a composition of images and sound related to a specific theme, such as 'nature'. Based on these selected data, the control means in the system control the display of the selected data in the medical environment. In the case of for example the 'nature'-theme, this means that a scene from nature is displayed with accompanying sounds, such as the ocean and the sound of waves. Throughout the examination, this scene and the sound will be provided to have a calming and relaxing effect on the patient. In this manner the patient will feel more comfortable during the examination.

An embodiment of a system according to the invention is characterized in that the data comprise visual data. These visual data can be seen by the patient during treatment and examination.

The visual data may comprise still images, such as for example photographs, but they may also comprise moving images.

An embodiment of a system according to the invention is characterized in that the display means comprise at least one projector for projecting the visual data on surfaces of the environment. In this manner the visual data can be projected on for example the walls of an examination room, or the ceiling or the floor, dependent on the preferences and the type of environment.

Furthermore, the system can also reproduce audio data together with, or separate from, the visual data, such as music, sound, or a human voice.

An embodiment of a system according to the invention is characterized in that the selection means comprise at least one identifier element comprising predetermined data, and the control means comprise reading means for reading the data comprised in the identifier.

The identifier element may comprise an identifier chosen from a group of radio frequency transponders and barcodes, and the reading means comprise a reader chosen from a group of radio frequency readers and barcode readers.

Advantageously, personal data of the person can be included in the collection of data. In this manner the patient is able for example to see and hear personal photographs, films and voices of his family during an examination, which further enhances the feeling of comfort which helps the patient relax.

Advantageously, the personal data can be sent via a public switching network to be included in the collection of data. Before going to the hospital, the patient can easily send his or her personal data via for example a personal computer connected to the Internet.

An embodiment of a system according to the invention is characterized in that the environment comprises one of a group of hospital rooms, including medical treatment rooms, medical examination rooms, waiting rooms, and patient recovery rooms.

The invention furthermore relates to a method of providing a personalized experience to a person in a medical environment, the method comprising the steps of offering the person a collection of data from which a selection may be made, and displaying data in the medical environment based on the selection made by the person.

An embodiment of a method according to the invention is characterized in that the patient is offered a collection of identifiers from which a selection may be made, each identifier comprising predetermined data which are readable by a reader comprised in the medical environment, to control the display of data in the environment.

Figure 3:
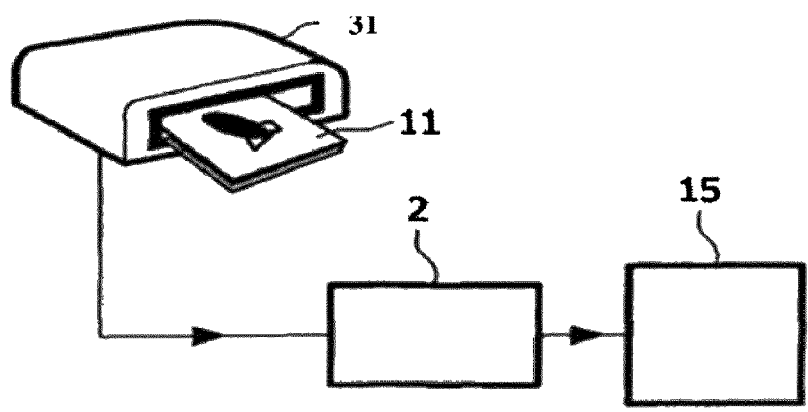
Figure 4:
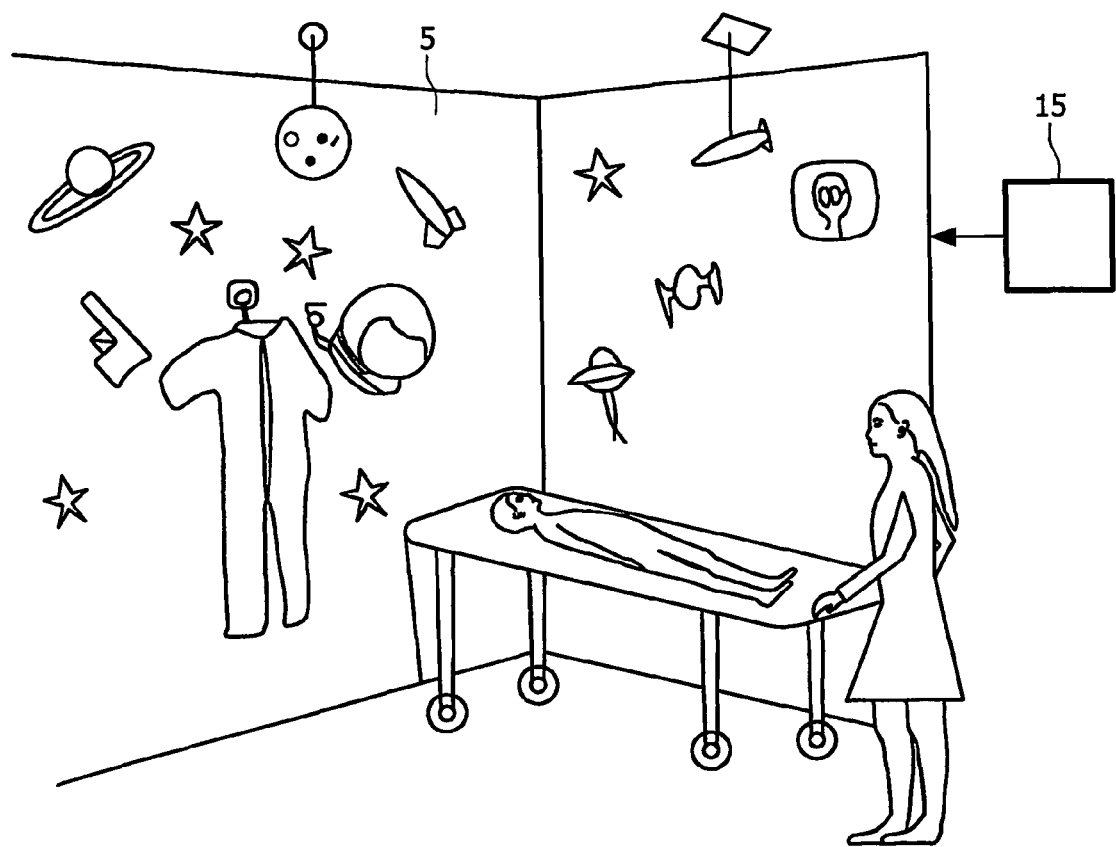
Figure 5A:
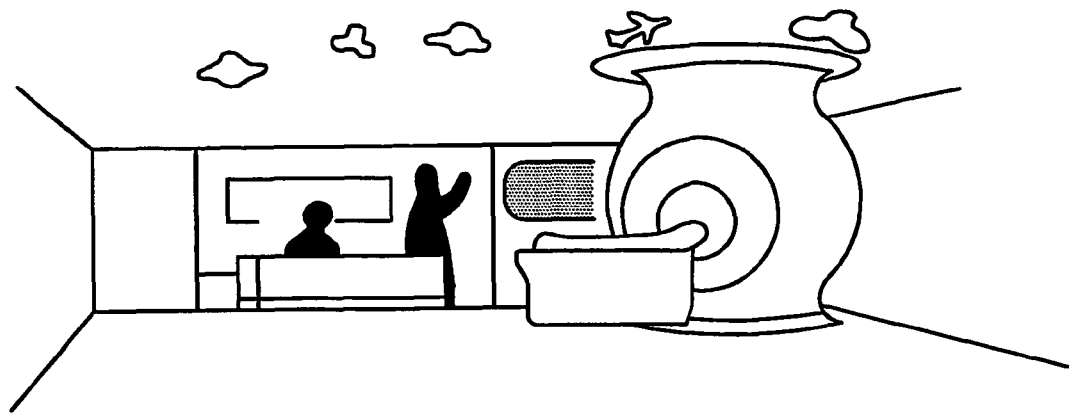
Figure 5B:
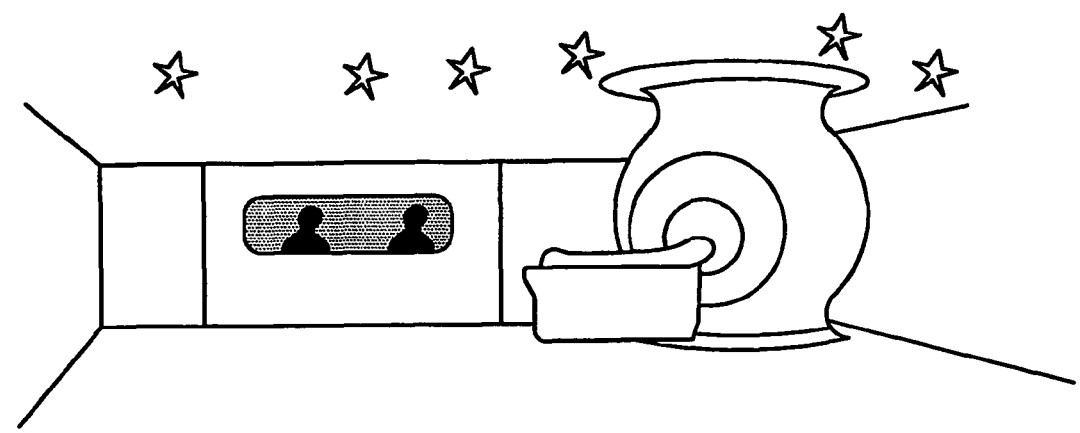

The invention will be described in more detail hereinafter with reference to the drawings, in which FIGS. 1 to 4 show a first embodiment of a system for providing a personalized experience to a person in a medical environment according to the invention, FIGS. 5*a* and 5*b* show a further embodiment of a system for providing a personalized experience to a person in a medical environment according to the invention.

Figure 2:
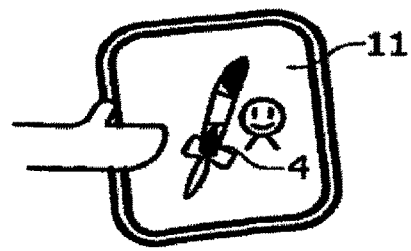

FIGS. 1, 2 and 3 show a first embodiment of a system for and method of providing a personalized experience to a person in a medical environment according to the invention. In FIG. 1, a patient, in this example a child-accompanied by his mother, enters a hospital and reports at the reception desk. After the relevant patient information with regard to the child has been processed, the child is offered data 1 from which a selection may be made via selection means. In this embodiment, the data are arranged in themes, such as for example 'aerospace', 'nature', 'animals' and 'cartoons'. The child selects a theme, based on his own personal preferences as can be seen in FIG. 2, the selection means comprise at least one identifier element 11 comprising predetermined data A, in this embodiment a radio frequency transponder comprising visual and audio data A relating to aerospace, such as pictures or a film of a rocket in space, astronauts, stars, moving planets, etc., and accompanying music.

As can be seen in FIG. 3, the control means 2 comprise reading means 3 for reading the data comprised in the identifier element 11, in this embodiment a radio frequency reader 31 provided in the wall in front of the entrance to a medical environment, in this embodiment an examination room 5. The child places the identifier element 11 in the reader 31, and enters the examination room 5. Based on the identifying data read by the reader, the control means 2 control display means 15 to display the data A in the examination room 5, based on the selection made by the child. In this embodiment, the visual and audio data relating to aerospace are thus reproduced in the examination room 5, as can be seen in FIG. 4. Throughout the examination, this scene and sound will be provided to have a calming and relaxing effect on the child. As a result, looking at and listening to his favorite theme, in this case aerospace, the child will feel more comfortable during the examination.

FIGS. 5a and 5b show a further embodiment of a system for providing a personalized experience to a person in a medical environment according to the invention. In this embodiment, the data that are displayed in the examination room comprise visual data related to both day and night. When the examination starts, a blue sky is projected on the ceiling of the room, accompanied by relevant sounds such as birds singing. When the examination proceeds, the sky changes from day to night, and a night sky with stars is projected accompanied by relevant sounds such as singing crickets. In this embodiment, the visual and audio data are indicative of the duration of the examination; as soon as the night sky disappears again and the blue sky appears, the examination is over. The patient is thus informed of the status of the examination via the data that are displayed in the environment.

It is noted that this can for example also take place via a voice informing the patient, a timer counting down, changing color of the lighting. Furthermore, the patient could be instructed via the displayed data, for example by clouds in the sky changing in numbers counting down the time; or for children, for example, a cartoon of a seal diving under water to indicate the time period the child should hold its breath during examination. It is furthermore possible to add a two-way video connection between patient and control room via for example a wall or the ceiling of the examination room.

It is furthermore noted that besides visual and audio data, also specific scents can be provided in the environment to further enhance the personalized experience. When the patient chooses for example a 'nature' theme, and a film of the ocean is projected, the scent of a sea breeze could be dispensed in the environment.

As settings in the environment can be personalized towards the patient's preference, the patient is helped to feel comfortable throughout the examination. The medical environment is experienced as more open and friendly, and the two-way audio/video communication gives the patient a more natural means of communication. In addition, the effect of the total experience on the patient serves to aid the clinical users in their everyday tasks. When the patient is relaxed and comfortable, they have to spend less time calming and reassuring patients, which further enhances efficiency of the workflow. Since the medical environment allows to improve workflow, the patient throughput is also increased.

It is furthermore advantageous also for the hospital to apply the system and the method according to the invention, because by offering a more "personal" experience, hospitals can attract more patients. Hospitals are enabled to express their values and specialties by creating a tailor-made experience befitting (?) the relevant hospital. By furthermore providing an innovative working environment, hospitals are able to attract and retain top class professionals.

The system according to the invention can be advantageously applied in the following described environment. In a certain department of a hospital, in this embodiment a radiology department, a waiting room, a changing room and a preparation room are merged into one room, referred to as Personal Preparation Room. This room provides a personal space for a patient during his stay in the radiology department By merging these three rooms into one, the possibility is furthermore created for family and friends to be with the patient until the beginning of the examination. The Personal Preparation Room can be personalized via the system for providing a personalized experience to a person in a medical environment according to the invention, for example by playing personally chosen music and displaying pictures as entertainment and relaxation means for the patient.

Before the examination procedure starts, the patient is provided with all relevant information, in a manner which suits the personally selected theme. The patient can for example be shown a themed presentation of the coming examination in a style which carries the chosen profile's elements. When the patient is for example a child, this can take place by telling a story in the form of a tale or using a cartoon system.

This personalized theme is continued in the examination room, as described before. The visual data may comprise for example pictures, a film, projected sentences for advise during treatment, and a video connection showing the doctor. The audio data may comprise for example music, spoken advise during treatment, and the actual voice of the doctor.

Through changes in lighting and audio solutions together with projections of images and/or animations that are initiated by the entrance of a person (professional or patient) in a radiology department (similar for cardiology, intensive care unit, etc.) a certain ambience/atmosphere is created in this specific architectural context. This ambience can be a choice from certain predefined themes (e.g. animal drawings for children or nature images) or truly personal when personal content (eg. images of family or vacation) is inserted in the system.

Furthermore, the invention is not limited to applications involving patients. The system according to the invention can also be advantageously applied in the medical environment where the medical staff members are active during their work, such as for example a control room. In this manner a more comfortable working environment is offered to the medical staff.

The invention claimed is:

1. A system for providing a personalized experience to a person in a medical environment, comprising:
   means for selecting by the person preferred data from a collection of data, the means for selecting comprising at least one identifier element comprising predetermined data, and the means for selecting being connected with
   means for controlling means for displaying the selected data in the medical environment, the means for controlling comprising means for reading the data comprised in the identifier element.

2. A system as claimed in claim 1, wherein the data comprise visual data.

3. A system as claimed in claim 2, wherein the visual data comprise still images.

4. A system as claimed in claim 2, wherein the visual data comprise moving images.

5. A system as claimed in claim 1, wherein the display means comprise at least one projector for projecting the visual data on surfaces of the environment.

6. A system as claimed in claim 1, wherein the data comprise audio data.

7. A system as claimed in claim 1, wherein the identifier element comprises an identifier chosen from a group of radio frequency transponders and barcodes, and the reading means comprise a reader chosen from a group of radio frequency readers and barcode readers.

8. A system as claimed in claim 1, wherein personal data of the person can be included in the collection of data.

9. A system as claimed in claim 1, wherein the personal data can be sent via a public switching network to be included in the collection of data.

10. A system as claimed in claim 1, wherein the environment comprises one of a group of hospital rooms, including medical treatment rooms, medical examination rooms, waiting rooms, and patient recovery rooms.

* * * * *